(12) United States Patent
Tong et al.

(10) Patent No.: US 8,580,134 B2
(45) Date of Patent: Nov. 12, 2013

(54) NANOTEXTURED COBALT-CHROMIUM ALLOY ARTICLES HAVING HIGH WETTABILITY AND METHOD OF PRODUCING SAME

(75) Inventors: Weidong Tong, Warsaw, IN (US); Lawrence Salvati, Goshen, IN (US); Stephanie Vass, Warsaw, IN (US)

(73) Assignee: DePuy Synthes Products, LLC., Raynham, MA (US)

( * ) Notice: Subject to any disclaimer, the term of this patent is extended or adjusted under 35 U.S.C. 154(b) by 96 days.

(21) Appl. No.: 12/754,340

(22) Filed: Apr. 5, 2010

(65) Prior Publication Data

US 2010/0268346 A1    Oct. 21, 2010

Related U.S. Application Data

(60) Provisional application No. 61/169,365, filed on Apr. 15, 2009.

(51) Int. Cl.
*C25F 3/00*    (2006.01)

(52) U.S. Cl.
USPC ................ 216/96; 216/83; 424/422; 424/423

(58) Field of Classification Search
USPC ................ 148/525; 216/108, 109, 56, 83, 96; 424/422, 426; 427/2.26, 2.27; 433/201.1; 525/333.7; 606/60; 623/1.45, 18.11, 20.14, 23.5, 23.55, 623/23.6, 23.76
See application file for complete search history.

(56) References Cited

U.S. PATENT DOCUMENTS

| | | | | |
|---|---|---|---|---|
| 4,678,523 A | * | 7/1987 | Sridhar et al. | 148/325 |
| 5,607,480 A | * | 3/1997 | Beaty | 623/23.5 |
| 2004/0167633 A1 | * | 8/2004 | Wen et al. | 623/23.57 |
| 2005/0251260 A1 | * | 11/2005 | Gerber et al. | 623/17.13 |
| 2006/0293758 A1 | * | 12/2006 | Yang et al. | 623/23.5 |

OTHER PUBLICATIONS

Research Discloser 293054, Process to enhance the adhesion of a polymer film to a steel alloy surface, Sep. 1988, p. 1.*

* cited by examiner

*Primary Examiner* — Duy Deo
*Assistant Examiner* — Erin Bergner

(57) ABSTRACT

The present invention relates to articles comprising a cobalt-chromium alloy and bearing a surface oxide layer that has a thickness of 20 to 40 Å, is enriched in chromium relative to said article, and includes a plurality of indentions that, independently, have a diameter of from about 40 to about 500 nm. Such articles can be suitable for implantation in a mammal.

10 Claims, 17 Drawing Sheets

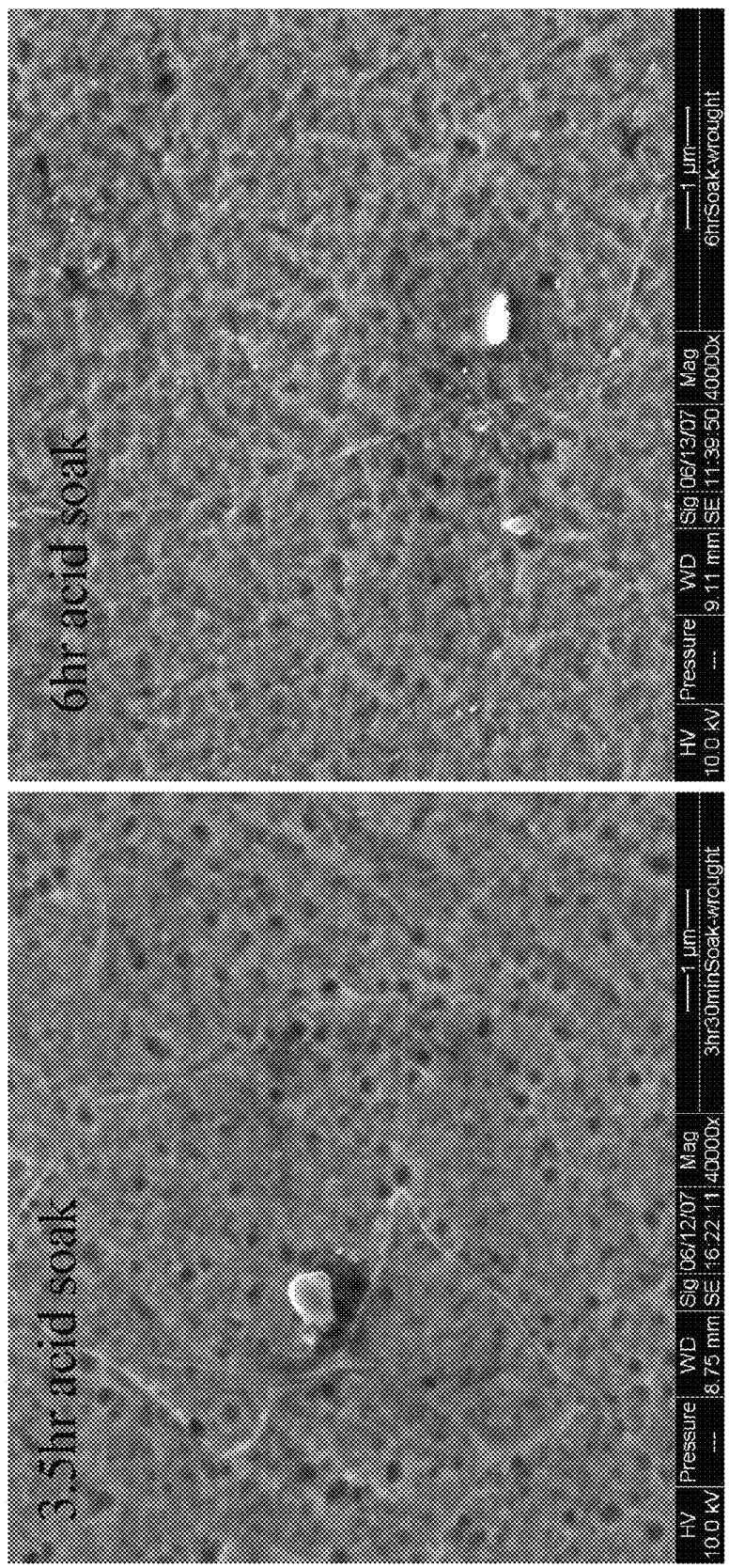

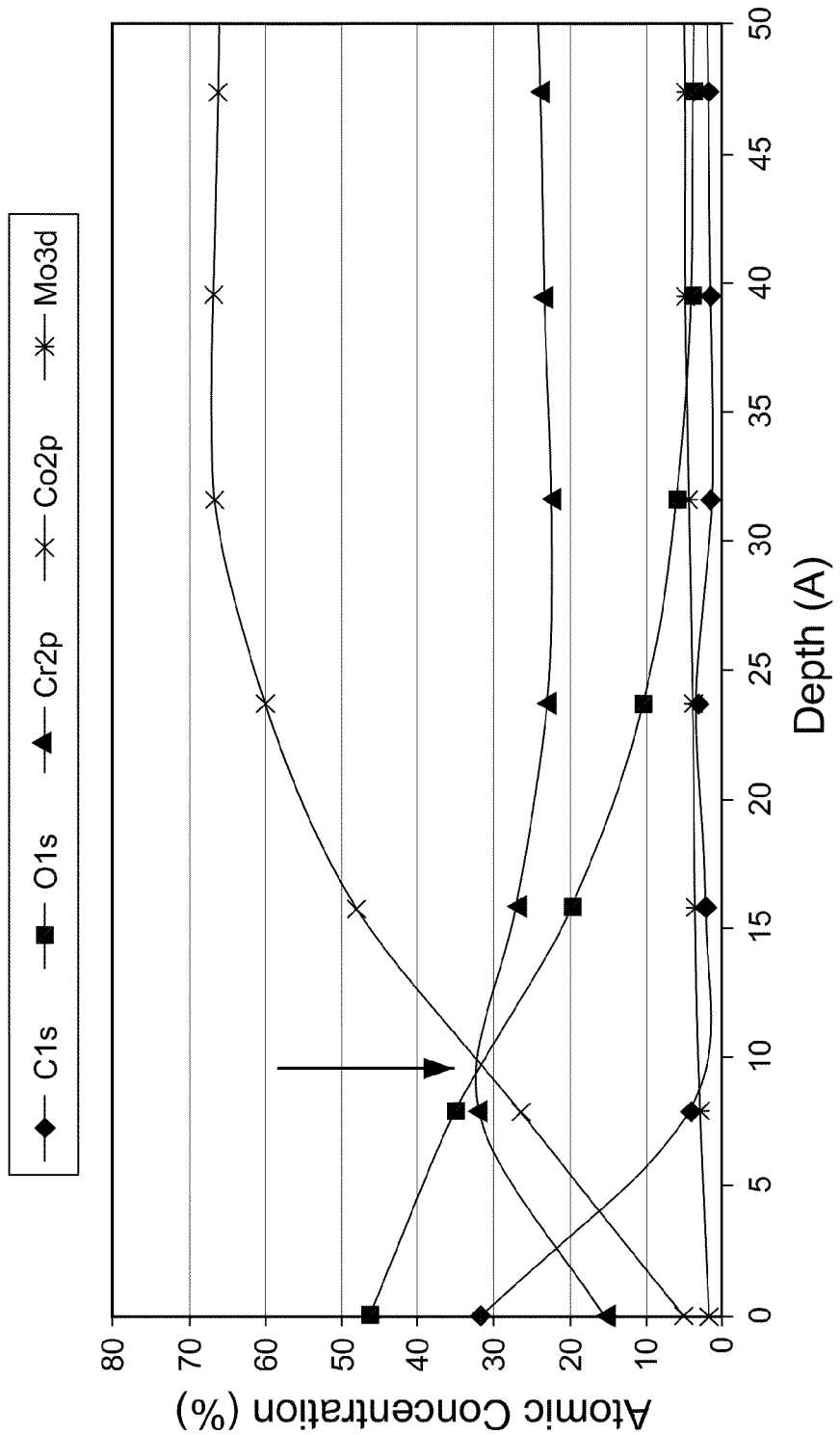

NANOTEXTURED COBALT-CHROMIUM ALLOY ARTICLES HAVING HIGH WETTABILITY AND METHOD OF PRODUCING SAME

CROSS REFERENCE TO RELATED APPLICATIONS

The present application claims benefit of U.S. Provisional Application No. 61/169,365, filed Apr. 15, 2009, which is related to the following three applications, which were all filed on the same day: (i) U.S. Patent Application No. 61/169,443 entitled "Micro and Nano Scale Surface Textured Titanium-Containing Articles and Methods of Producing Same," having inventors Weidong Tong and Larry Salvati; (ii) U.S. patent application Ser. No. 12/424,000, entitled "Methods and Devices For Bone Attachment," having inventors Weidong Tong and Larry Salvati; and (iii) U.S. patent application Ser. No. 12/424,049, entitled "Methods and Devices For Implants With Calcium Phosphate," having inventors Weidong Tong, Larry Salvati and Pooja Kadambi. Each of the aforementioned applications are hereby incorporated herein by reference in their entirety.

TECHNICAL FIELD

The invention concerns, inter alia., nanotextured articles made from cobalt chromium alloy and having high wettability and methods for making and using same.

BACKGROUND

There are a number of design criteria which have long been sought for segmental bone replacement implants including (1) the implant should last the lifetime of the patient without losing function or initiating any adverse process response; (2) the implant should restore the normal function of the bone in which it is implanted; and (3) the implant should be producible on a commercial scale. To satisfy the foregoing criteria, not only should the implant support the imposed load, often of a fluctuating nature, but the interface between the implant and the bone should also withstand the load requirement.

A plastic cement such as polymethyl methacrylate is often used to affix an implant to bone as well as to improve the fit between the implant and the bone. Implants also have been provided with porous coatings which mate with the bone and invite bone ingrowth such that, after a period of time, the prosthesis becomes integrated into the bone structure. Typical of such coatings are the those disclosed in U.S. Pat. Nos. 3,855,638; 4,206,516; 4,156,943; and 4,612,160.

Ceramic coatings have also been used to good effect and often are particularly desirable because of the affinity between bone and ceramic materials such as alumina ($Al_2O_3$). Typical of such coatings are those disclosed in U.S. Pat. Nos. 4,145,764 and 4,483,678 to which are particularly concerned with dental implants, and U.S. Pat. Nos. 4,309,488 and 4,846,837, which more broadly disclose implantable bone replacement material for use throughout the body.

Other work has utilized highly convoluted surfaces on the implant. U.S. Pat. Nos. 5,368,881 and 5,658,333 show use of non-spherical powder to produce a roughened surface for prosthesis. These surfaces, however, are known to have little to no inter-connected porosity.

There is a continued need in the art for prosthesis surfaces with improved properties.

SUMMARY

One aspect of the present invention concerns articles suitable for implantation in a mammal which comprise cobalt-chromium alloy and bear a surface oxide layer that has a thickness of 20 to 40 Å, is enriched in chromium relative to said article, and includes a plurality of indentions that, independently, have a diameter of from about 40 to about 500 nm. In some embodiments, the layer has a liquid absorbing capacity of at least about 50 $\mu$l/in$^2$. In some articles, the cobalt-chromium alloy is CoCrMo. In some embodiments, the surface of said article comprises cobalt-chromium alloy beads.

Other aspects of the invention concern methods for making nanotextured articles having high wettability. Some articles have properties as described above. Some methods comprise contacting an article that includes cobalt chromium alloy with a solution comprising hydrochloric acid for a time and at a temperature effective to form a surface oxide layer on said article that has a thickness of 20 to 40 Å, is enriched in chromium relative to said article, and includes a plurality of indentions that, independently, have a diameter of from about 40 to about 500 nm. In certain preferred embodiments, the solution is substantially free of oxidizing agent.

In some processes, the solution has a concentration of $H^+$ of at least about 4 M and a concentration of $Cl^-$ of at least about 4 M. The solution can further comprise a chloride-containing compound at a concentration in the range of about 0.01M to 8M. In some embodiments, the solution has a concentration of $H^+$ of about 0.8 to about 12 M and a concentration of $Cl^-$ that is greater than said concentration of $H^+$. Preferred chloride-containing compounds include sodium chloride (NaCl), potassium chloride (KCl), calcium chloride ($CaCl_2$), ammonium chloride ($NH_4Cl$), ferric chloride ($FeCl_3$), ferrous chloride ($FeCl_2$), cobalt chloride ($CoCl_2$), magnesium chloride ($MgCl_2$) and mixtures thereof.

In some process of the invention, the article is contacted with the solution at a temperature of about 20 to about 100° C. In certain processes, the article is contacted with the solution at a temperature of about 20 to about 40° C. The article is contacted with the solution for about 30 minutes to about 96 hours in some processes.

In yet other aspects, the article is suitable for implantation into a mammal. Some articles are a joint replacement prosthesis or component thereof. Certain articles are a hip or knee replacement prosthesis.

Still other aspects of the invention concern implanting the article of claim 1 into a mammal, such as a human.

DETAILED DESCRIPTION OF ILLUSTRATIVE EMBODIMENTS

Figure 1A:
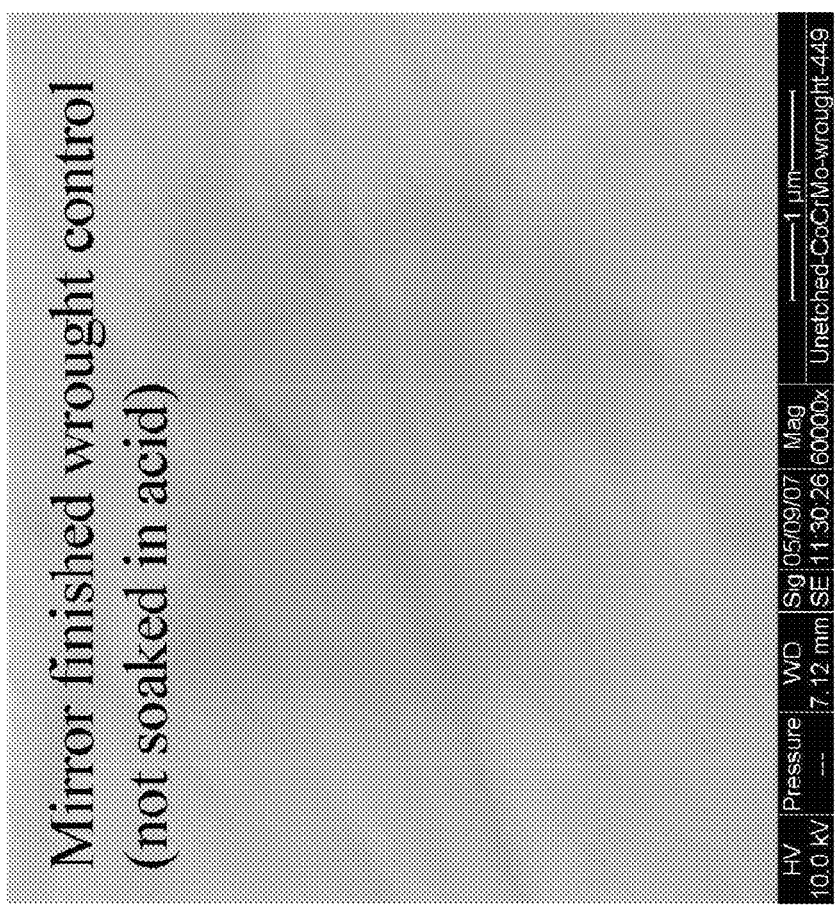
FIG. 1 shows the images of a ¾" (diameter) polished wrought CoCrMo (ASTM F1537) disk and those soaked for 5 min, 30 min, 1 h, 1.5 h, 3.5 h, 6 h, and 18 h in 8N HCl.
Figures 1B, 1C:
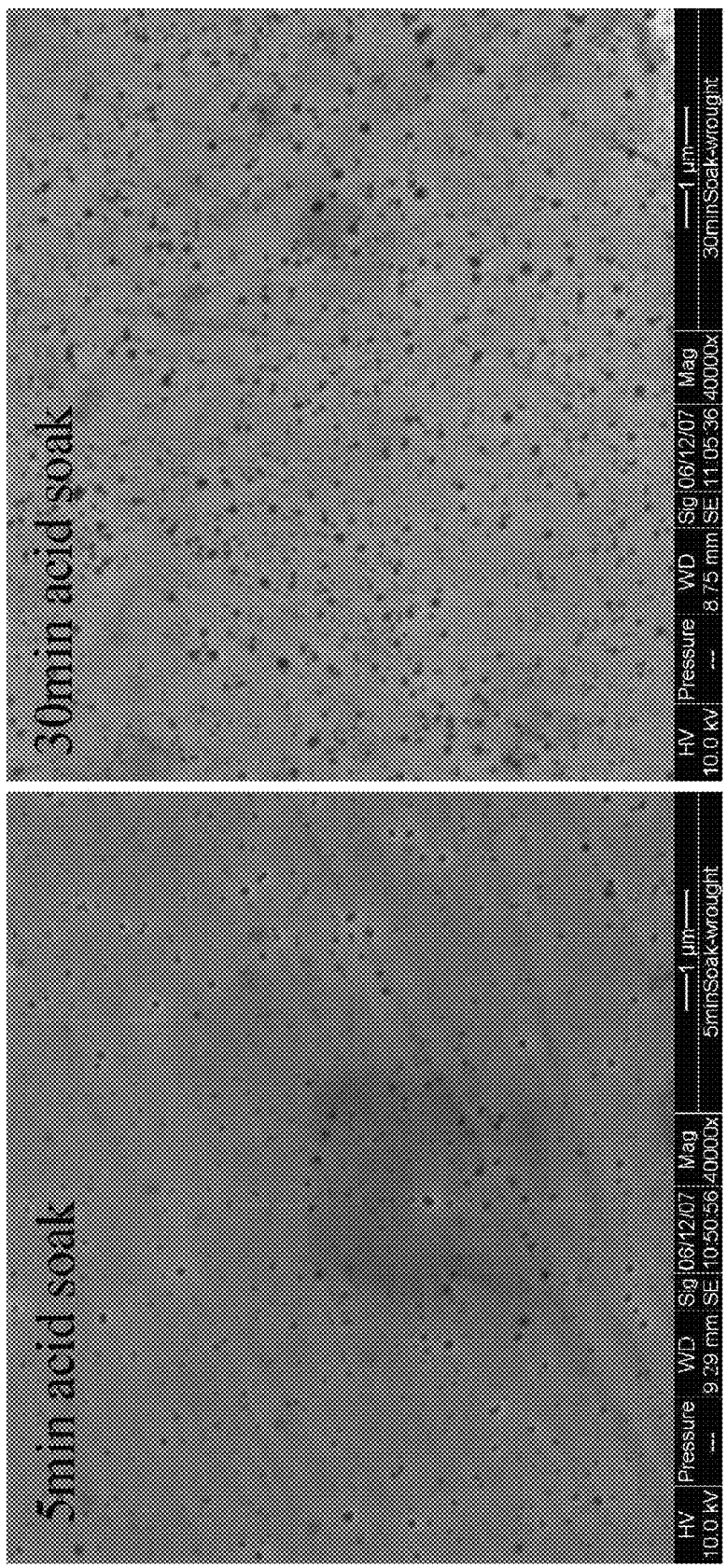
Figures 1D, 1E:
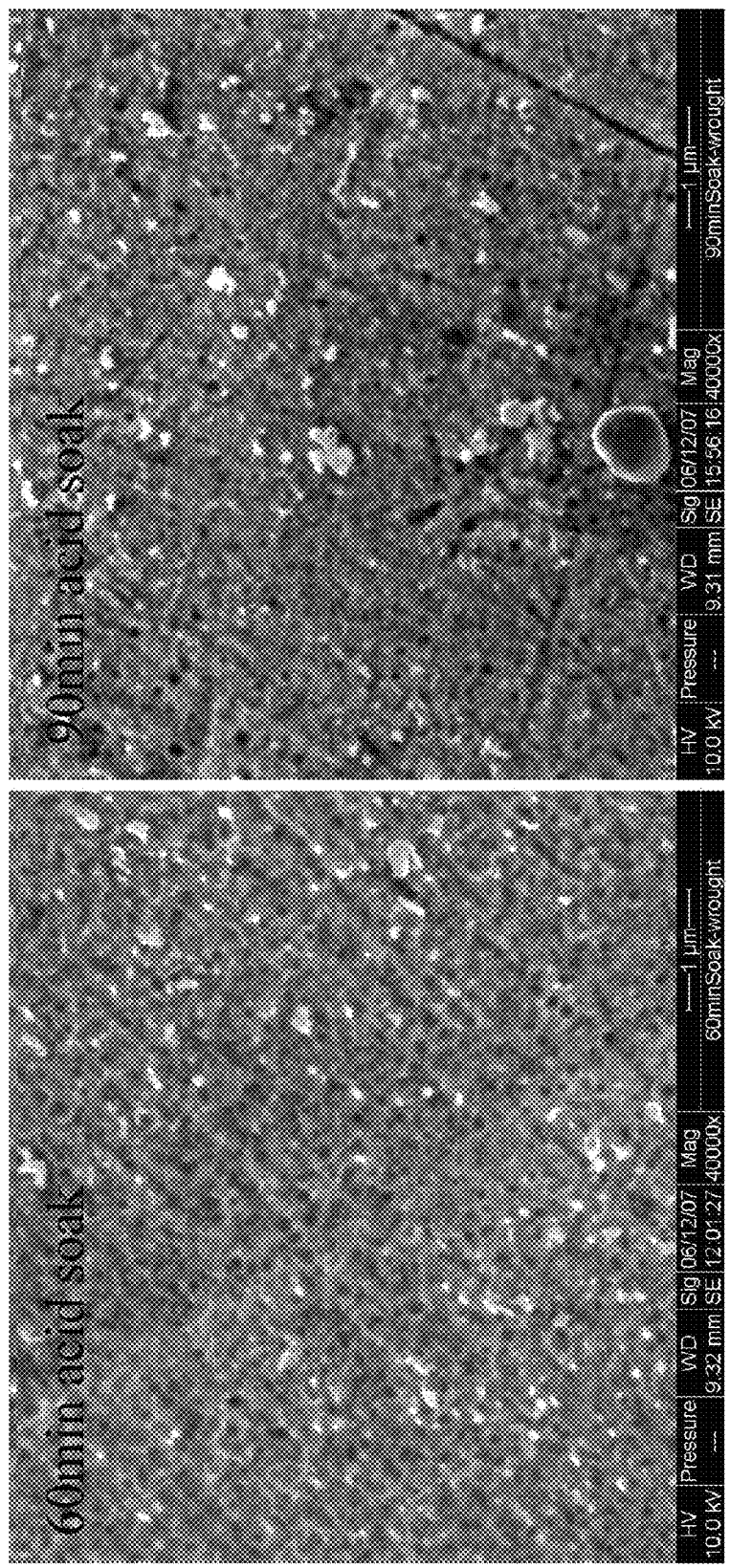
Figure 1H:
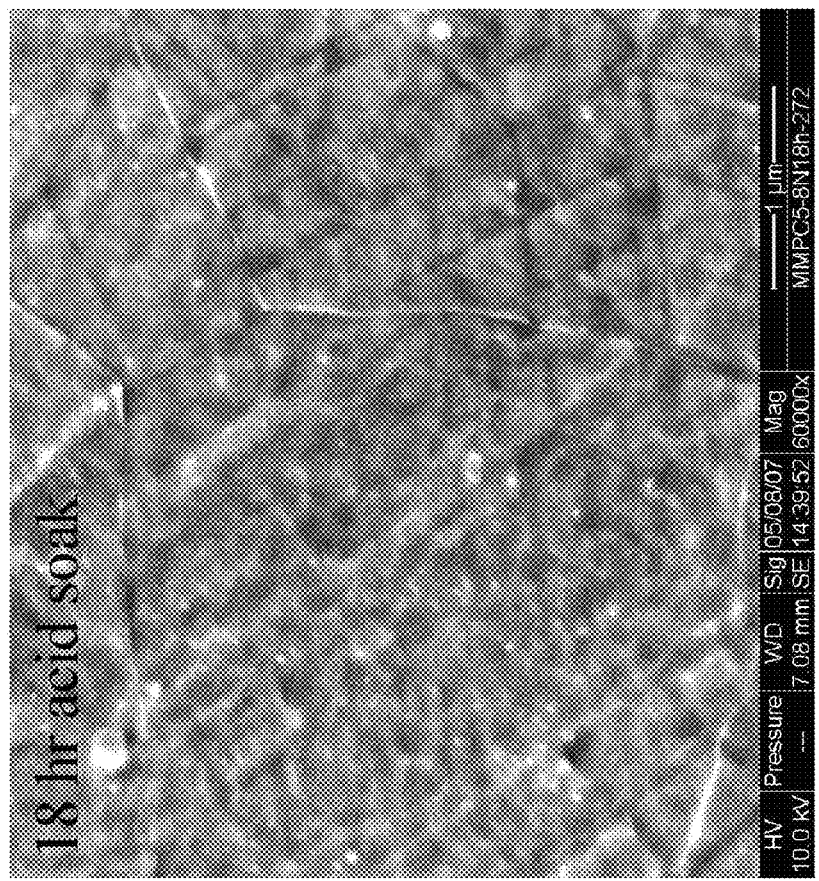
Figure 2B:
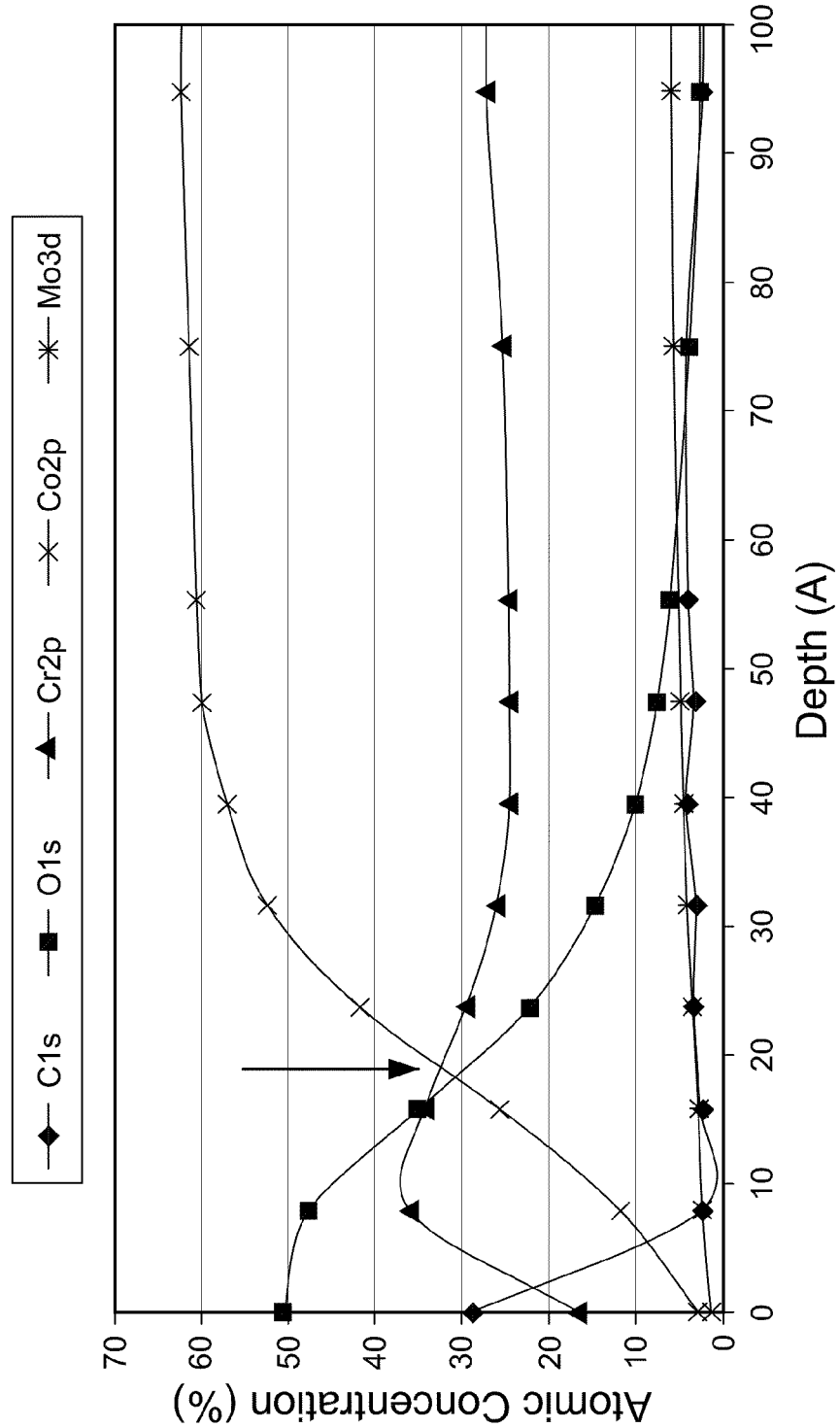
FIG. 2 shows the change in depth profile (by XPS) on (A) a polished wrought CoCrMo disk (not soaked in 8N HCl); and after soaking in 8N HCl (room temperature) for (B) 5 min, (C) 30 min, (D) 1 hr, (E) 1.5 h; (F) 6 h and (G) 24 h.
Figure 2C:
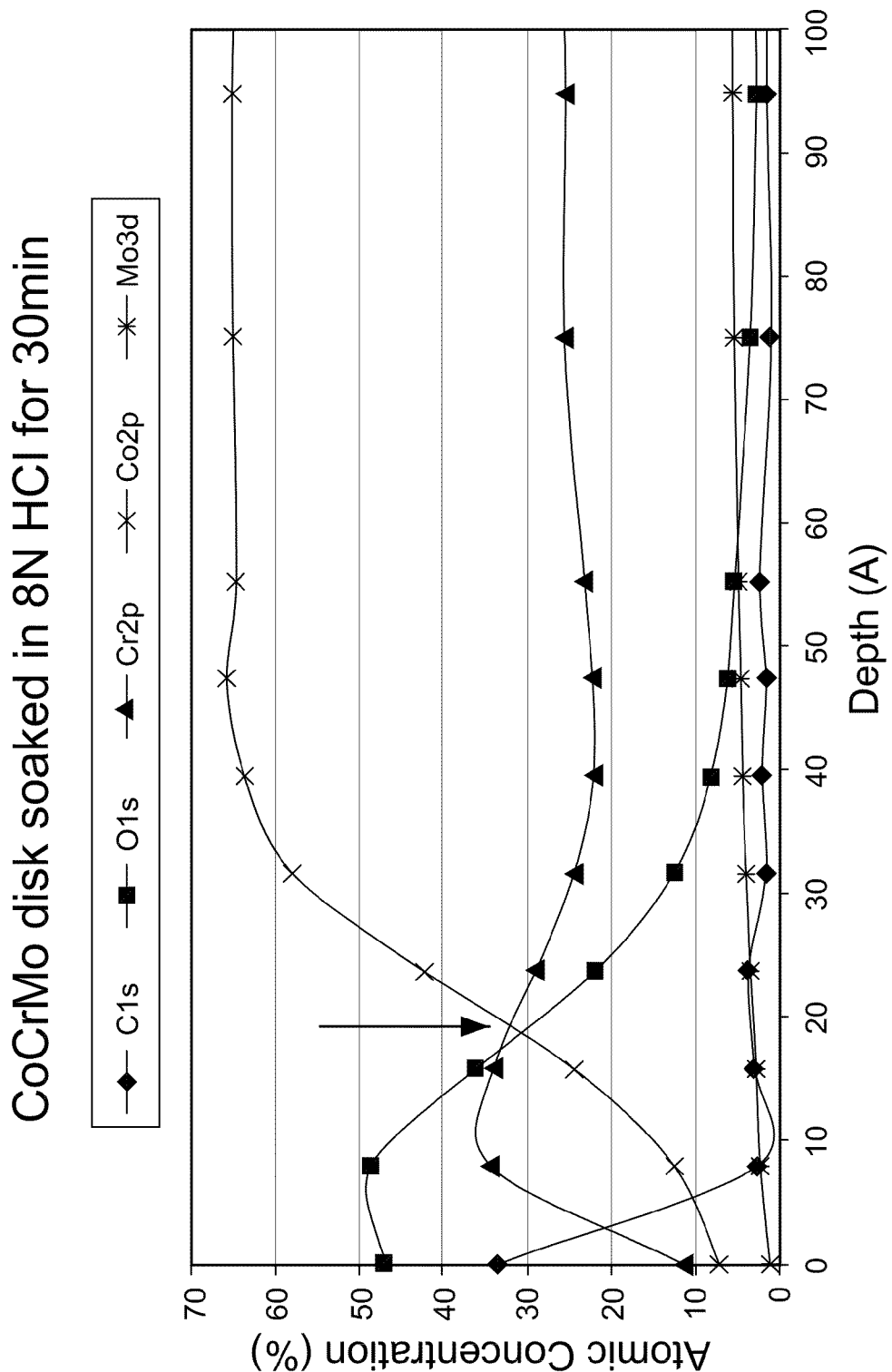
Figure 2D:
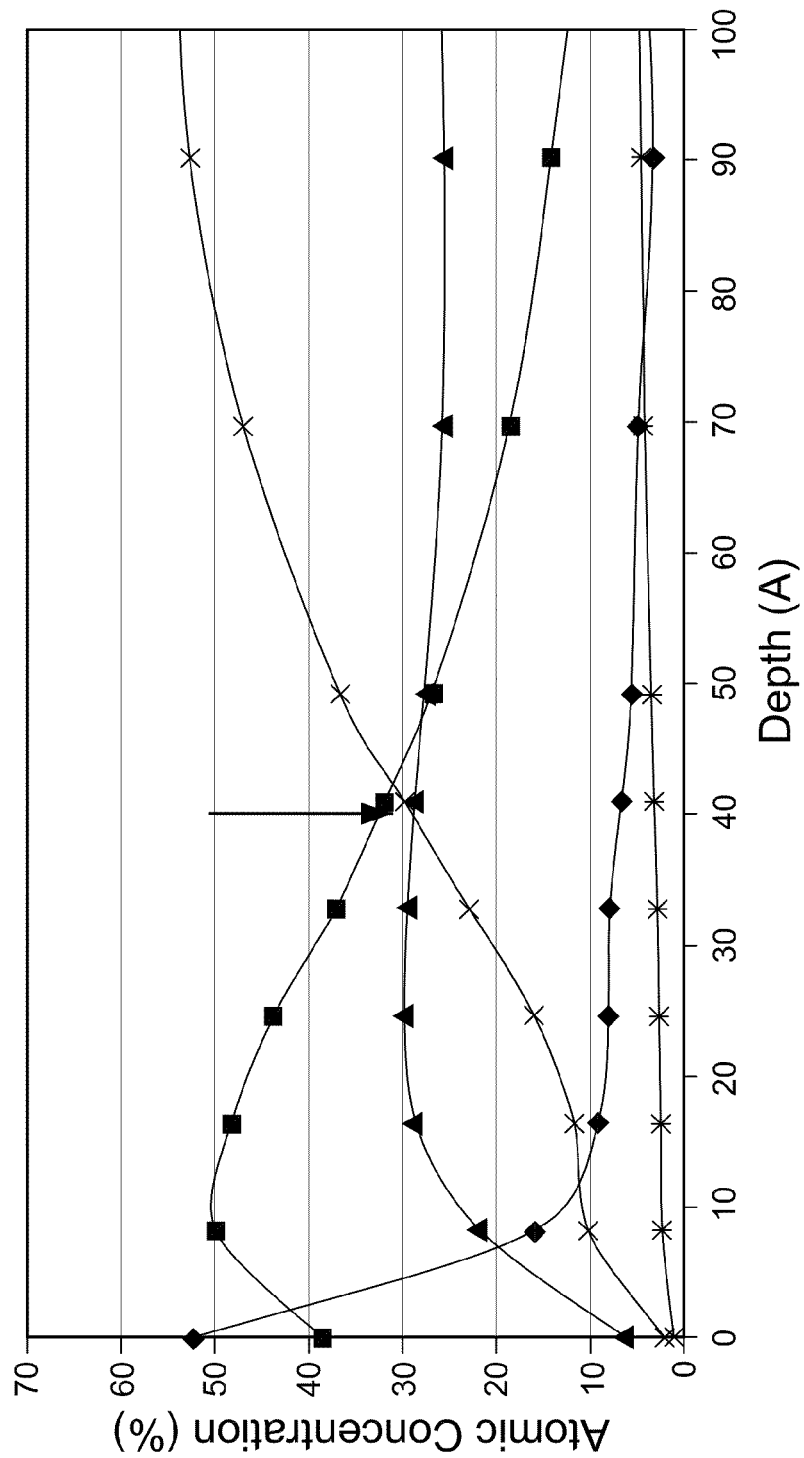
Figure 2E:
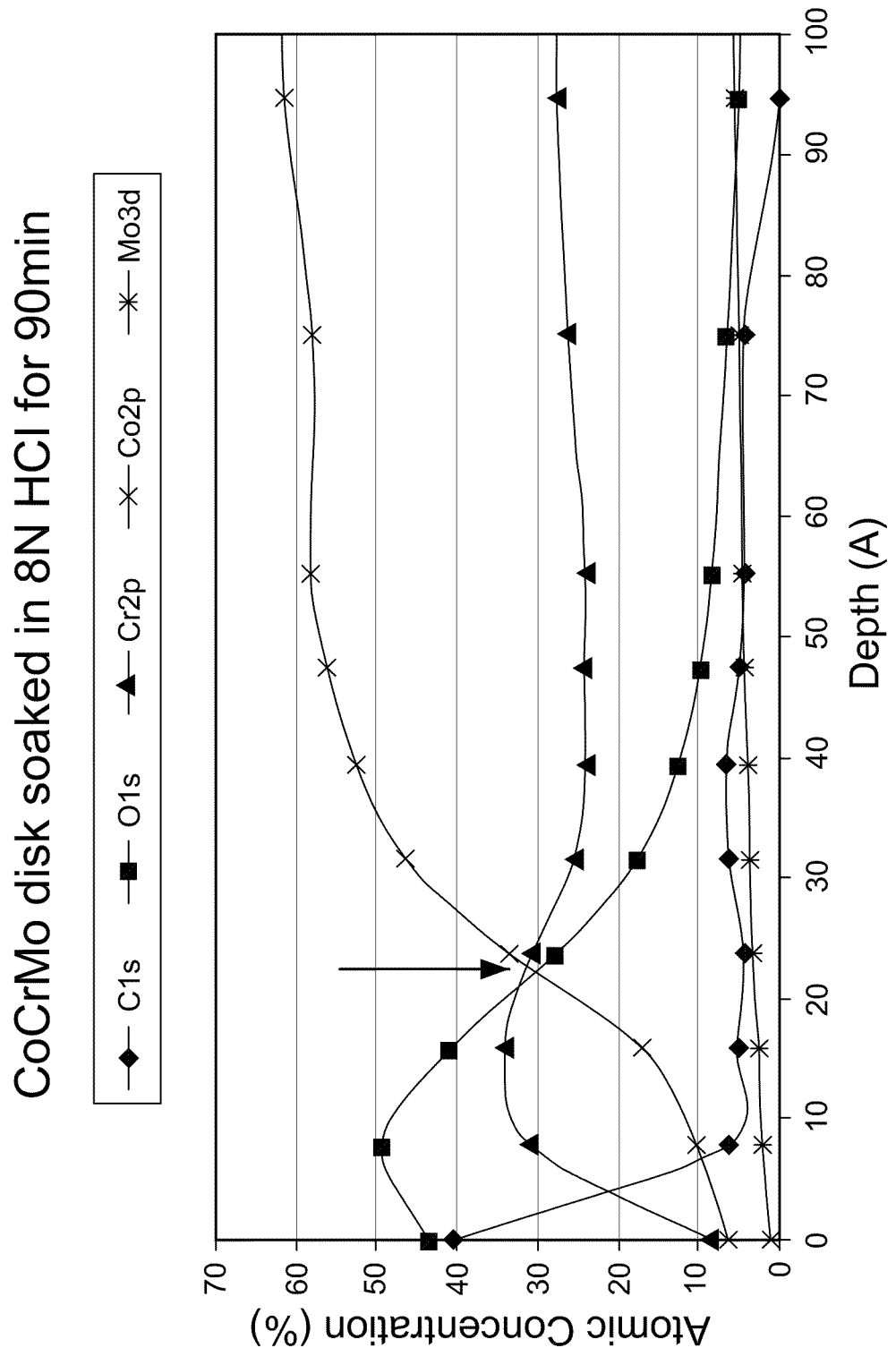
Figure 2F:
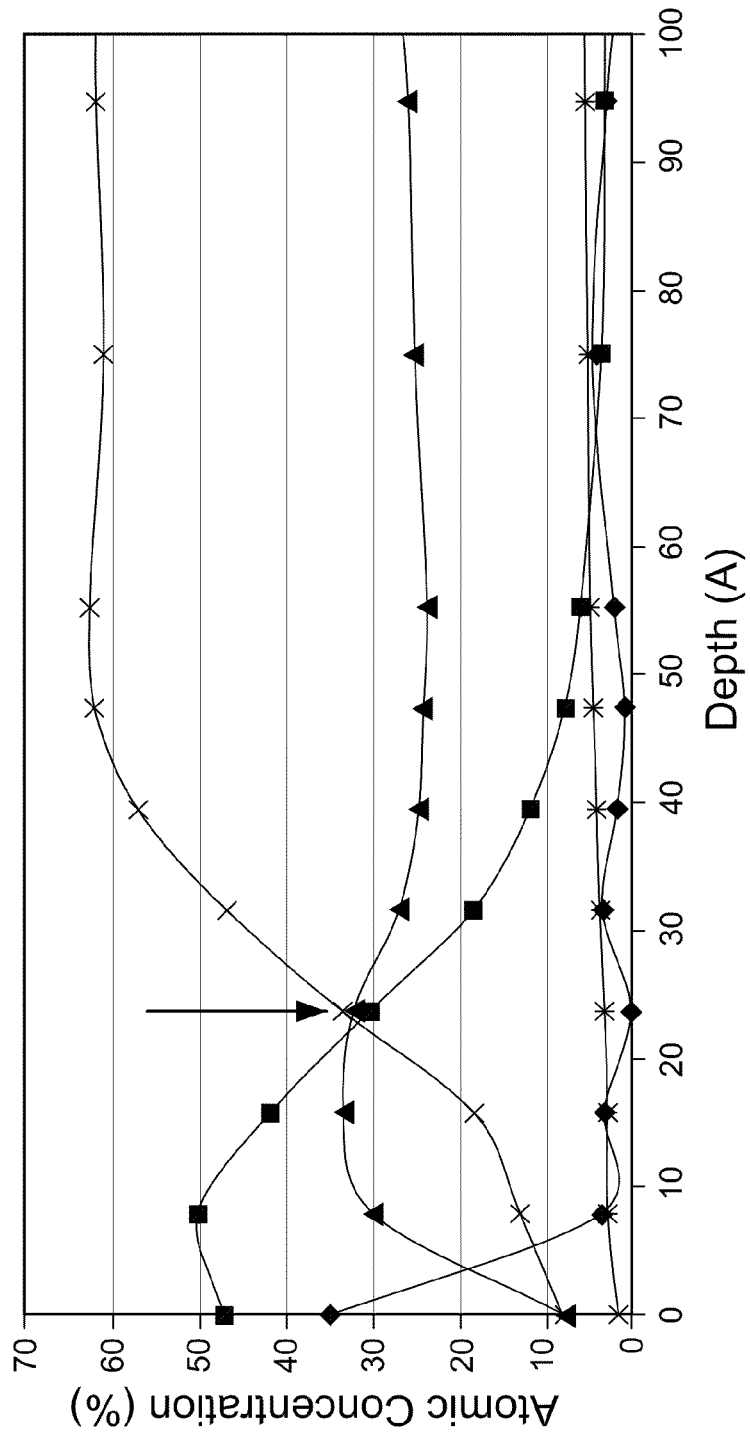
Figure 2G:
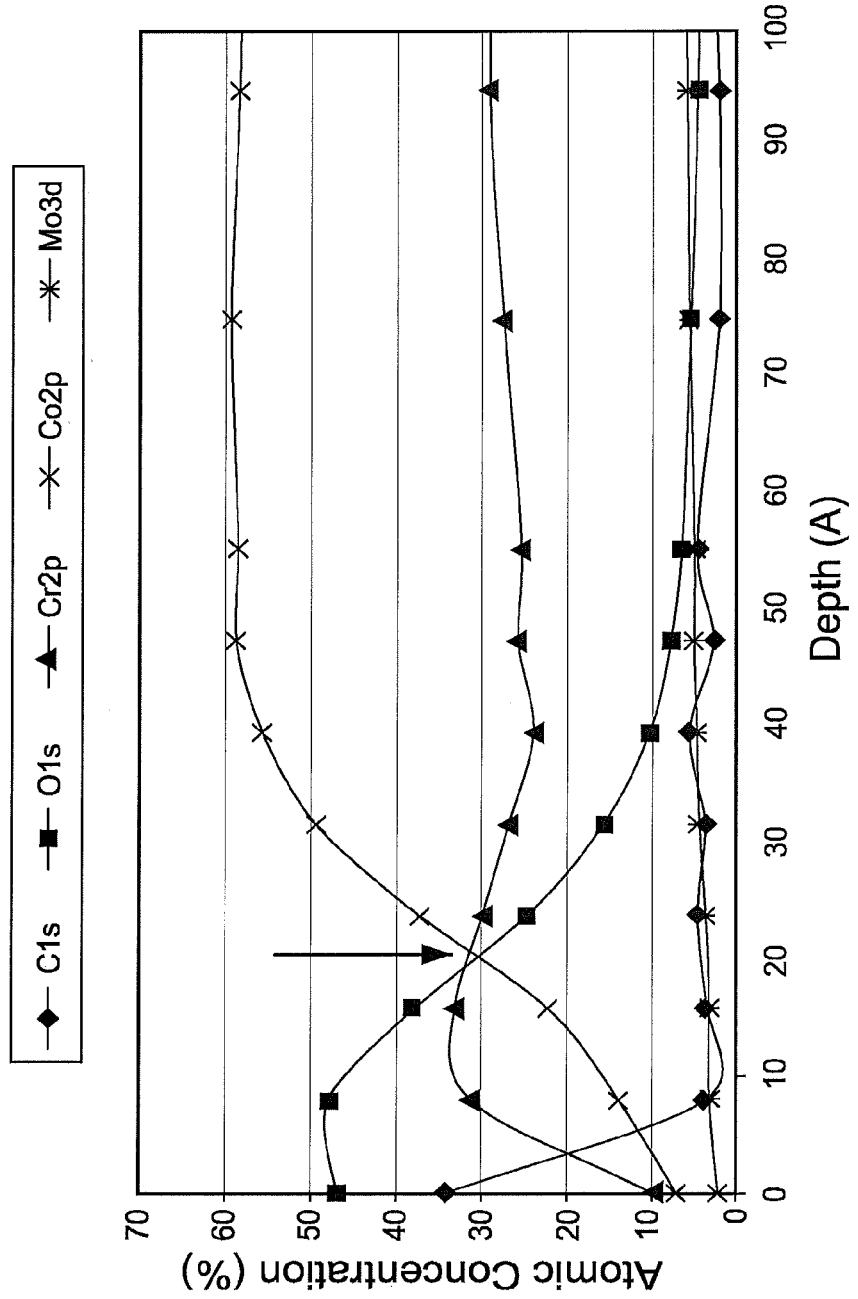

Surface properties of implant materials have an important role in the adhesion of adjacent cells to the implant. Wettability is one factor that is believed to impact the adhesion to the implant. By using the methods of the instant invention, the surface chemistry of the CoCrMo articles became chromium enriched. In addition, the surface became nanotextured and showed enhanced water absorbability. In some embodiments, a 3-10 fold improvement in water absorption is observed for the treated implant surfaces versus untreated surfaces. Implants made of such material show improved bone ingrowth.

One aspect of the present invention concerns articles suitable for implantation in a mammal which comprise cobalt-chromium alloy and bear a surface oxide layer that has a thickness of 20 to 40 Å, is enriched in chromium relative to said article, and includes a plurality of indentions that, independently, have a diameter of from about 40 to about 500 nm. In some embodiments, the layer has a liquid absorbing capacity of at least about 50 µl/in$^2$.

Liquid absorbing capacity is determined by measuring the amount of water absorbed into the article. The article whose liquid absorbing capacity is to be determined is weighed. Seven drops of 10 µl RO water (a total of seven spots and a total of 70 mg water) are placed on the article. The water is allowed to equilibrate for 5 minutes and then the top surface of the article is contacted by filter paper to remove any water remaining on the Porocoat® surface. Then, the weight of the Porocoat® disk is measured again. The difference of weight is converted to volume (1 mg water=1 µl)). The liquid absorbing capacity is determined by dividing the volume of water by the projected surface area of the article. In some embodiments, the liquid absorbing capacity is reported in µl/in$^2$.

Some articles of the invention have a liquid absorbing capacity of at least about 50 µl/in$^2$. Other articles have a liquid absorbing capacity of at least about 75 µl/in$^2$ or 100 µl/in$^2$.

If desired, liquid absorbing capacity can be compared to a standard such as DePuy's standard Porocoat® disk (¾" in diameter, 750µ thick, and 40-50% porosity). If the article is highly wettable, the water usually wicks into the article within 5 minutes. If the article is not highly wettable, the water usually beads up on the surface.

Some preferred metal objects include those comprising at least one of cobalt, chromium, and molybdenum, such as wrought CoCrMo. In some articles, the cobalt-chromium alloy is CoCrMo. In some embodiments, the surface of said article comprises cobalt-chromium alloy beads.

Other aspects of the invention concern methods for making nanotextured articles having high wettability. Some articles have properties as described above. Some methods comprise contacting an article that includes cobalt chromium alloy with a solution comprising hydrochloric acid for a time and at a temperature effective to form a surface oxide layer on said article that has a thickness of 20 to 40 Å, is enriched in chromium relative to said article, and includes a plurality of indentions that, independently, have a diameter of from about 40 to about 500 nm. In certain preferred embodiments, the solution is substantially free of oxidizing agent.

In some processes, the solution has a concentration of $H^+$ of at least about 4 N and a concentration of $Cl^-$ of at least about 4 N. The solution can further comprise a chloride-containing compound at a concentration in the range of about 0.01N to 8N. In some embodiments, the solution has a concentration of $H^+$ of about 0.8 to about 12N and a concentration of $Cl^-$ that is greater than said concentration of $H^+$. Preferred chloride-containing compounds include sodium chloride (NaCl), potassium chloride (KCl), calcium chloride ($CaCl_2$), ammonium chloride ($NH_4Cl$), ferric chloride ($FeCl_3$), ferrous chloride ($FeCl_2$), cobalt chloride ($CoCl_2$), magnesium chloride ($MgCl_2$) and mixtures thereof.

The article can be contacted with the solution at any temperature suitable for modifying the surface. In some embodiments, the article is contacted with the solution at a temperature of about 20 to about 100° C., or in some embodiments, at a temperature of about 20 to about 40° C. The article can be contacted with the solution for a time sufficient to provide the desired surface properties. In some processes, for example, the article is contacted with the solution for about 30 minutes to about 96 hours in some processes. In other processes, the article is contacted with the solution for about 1 to about 36 hours.

The articles described herein are suitable for implantation into a mammal. Certain of these articles are prosthesis devices, such as a joint replacement prosthesis or component thereof. These devices include hip or knee replacement prosthesis.

The invention also concerns implanting the articles described herein into a mammal. In some embodiments, the articles are suitable for implant in humans.

Porocoat® Porous Coating is a three-dimensional, beaded coating marketed by DePuy Orthopaedics, Inc. In some embodiments, the coatings comprise a CoCrMo material.

The invention is illustrated by the following examples that are intended to be illustrative and not limiting.

EXAMPLES

The Disks

The mirror polished ASTM F1537 wrought CoCrMo disk, ¾" in diameter, was used for weight loss assessment and contact angle measurement. Such disks are available by machine cut from a bar stock (ASTM F1537 wrought) and a mirror polished finish (Ra<0.1µ). CoCrMo Porocoat® contains spherical beads of CoCrMo with sizes ranging approximately 150-250µ. The Porocoat® has a thickness of 750µ and a diameter of ¾" with a porosity ranging from 40-50%. The acid soaking test was carried out at room temperature/condition (18° C. to 23° C.). For a flat ¾" disk, a volume of at least 30 ml of the acid solution was used; for a ¾" Porocoat® disk, a volume of at least 50 ml of the acid solution was used.

Acid Solutions 100 mL of 12 N HCl was diluted with 50 mL of reverse osmosis (RO) treated water to produce an 8N HCl solution (Solution 1).

100 mL of 12 N HCl was diluted with 100 mL of reverse osmosis (RO) treated water to produce a 6N HCl solution (Solution 2).

100 mL of 12 N HCl was diluted with 200 mL of reverse osmosis (RO) treated water to produce a 4N HCl solution (Solution 3).

The chloride supplemented 1N HCl is prepared by adding 70 g of $CaCl_2.2H_2O$ in 100 ml of 1N HCl. The final concentrations in the chloride supplemented HCl acid are approximately [$H^+$]=0.8 N, [$Cl^{-1}$]=8.8 N, [$Ca^{2+}$]=4 N (solution 4).

Ultrasound cleaning: after completing each acid soaking time, each of the test sample was rinsed in RO water and followed ultrasound cleaning in RO for 20 minutes, 10 minutes and 5 minutes. The samples were then blow dry with nitrogen and thermally dried at 60° C. oven for at least 2 hours.

The etching studies utilized ¾" inch polished wrought CoCrMo disks (ASTM F1537) with Ra<0.1μ to measure weight loss during acid soaking process. The etching studies utilized 1" inch polished wrought CoCrMo disks (ASTM F1537) to measure contact angles. The etching studies utilized ¾" inch Porocoat® disks (ASTM F1537) to measure water absorbability.

Example 1

300 ml of Solution 1 was added to a 500 mL beaker. A ¾" inch diameter polished wrought CoCrMo disk was added to the teflone fixture so that only the polished surface was exposed to the acid and allowed to lie vertically. The top of the beaker was sealed with Parafilm. After soaking for the designated time, the disks were rinsed with running RO water and ultrasound cleaned. The experiment was repeated with 5 min, 30 minutes, 1 h, 1.5 h, 3.5 h, 6 h, 18 or 24 h soaking Micrographs of a control disk (not soaked) and the 5 min, 30 min, 1.5 h, 3.5 h, 6 h and 18 h soaked disks are presented in FIG. 1. In FIG. 2, the depth profiles of a polished disk and those soaked in 8N HCl for 5 min, 30 min, 1 h, 1.5 h, 6 h and 24 h.are presented. The depth distribution of Co, Cr, Mo, O, C from the top of the surface was examined by X-ray photoelectron spectroscopy (XPS). Five elements were examined (C1s, O1s, Co2p, Cr2p and Mo3d) at Pass Energy of 224.00 EV and step size 0.4 EV. Using Argon at a sputter setting of 2 kv2×2 the 200 μm×200 μm (200u45w15 kv) area was sputtered for a total of 2.1 minutes. The sputter cycles included 6 cycles at 0.1 min and 6 cycles at 0.2 min in Alternate Sputter Mode and have a total analysis time of 57 minutes. The depth of the Cr rich layer is defined by the intersection of the Cr and Co depth (indicated by arrows)

Figure 3A:
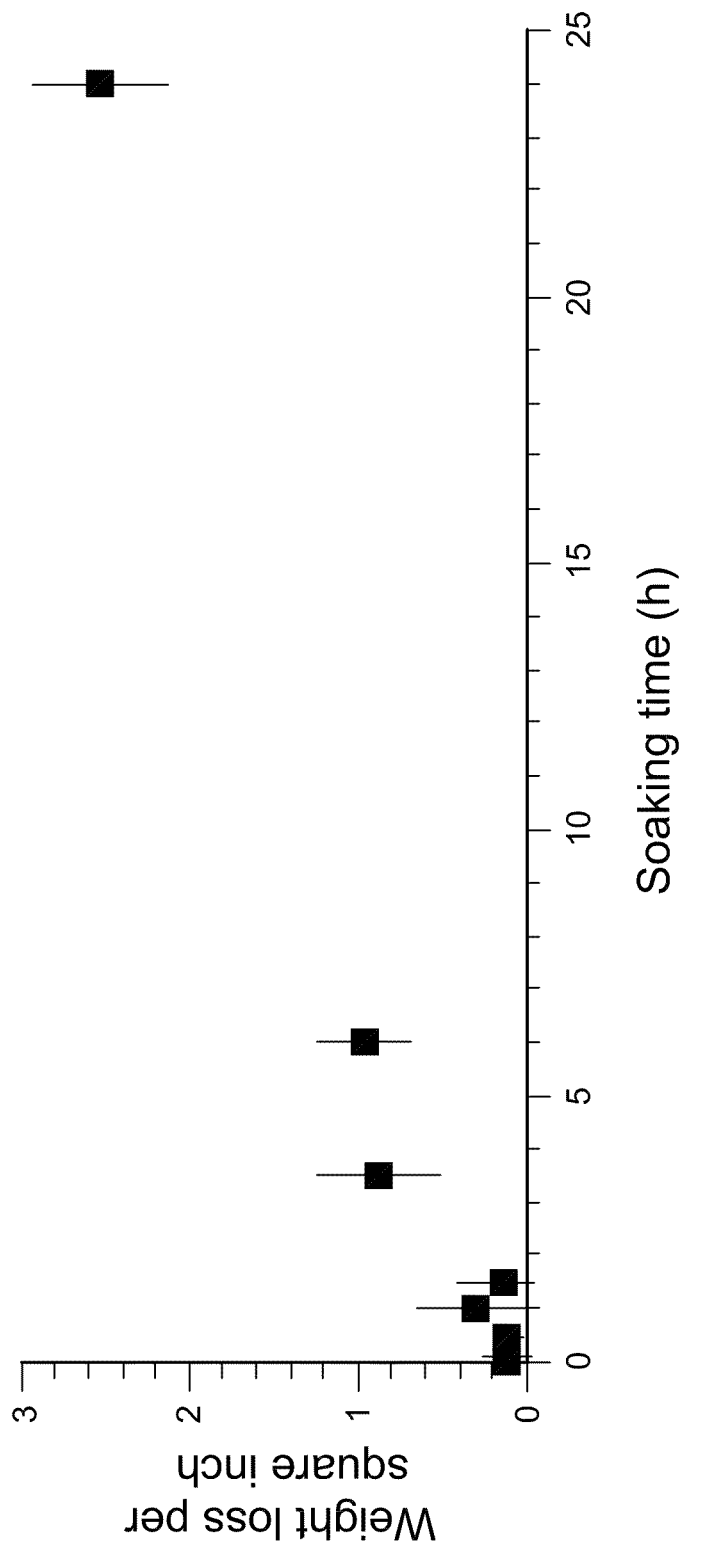
FIG. 3 (all disks were treated in 8N HCl for 24 hours at room temperature) shows (A) the weight loss per unit area over acid soaking time on ¾" (diameter) polished wrought CoCrMo disks, (B) the contact angle of water placed on the surface of the polished wrought disk versus acid soaking time, and (C) the water absorbability of the ¾" (diameter) Porocoat® disks versus acid soaking time.
Figure 3B:
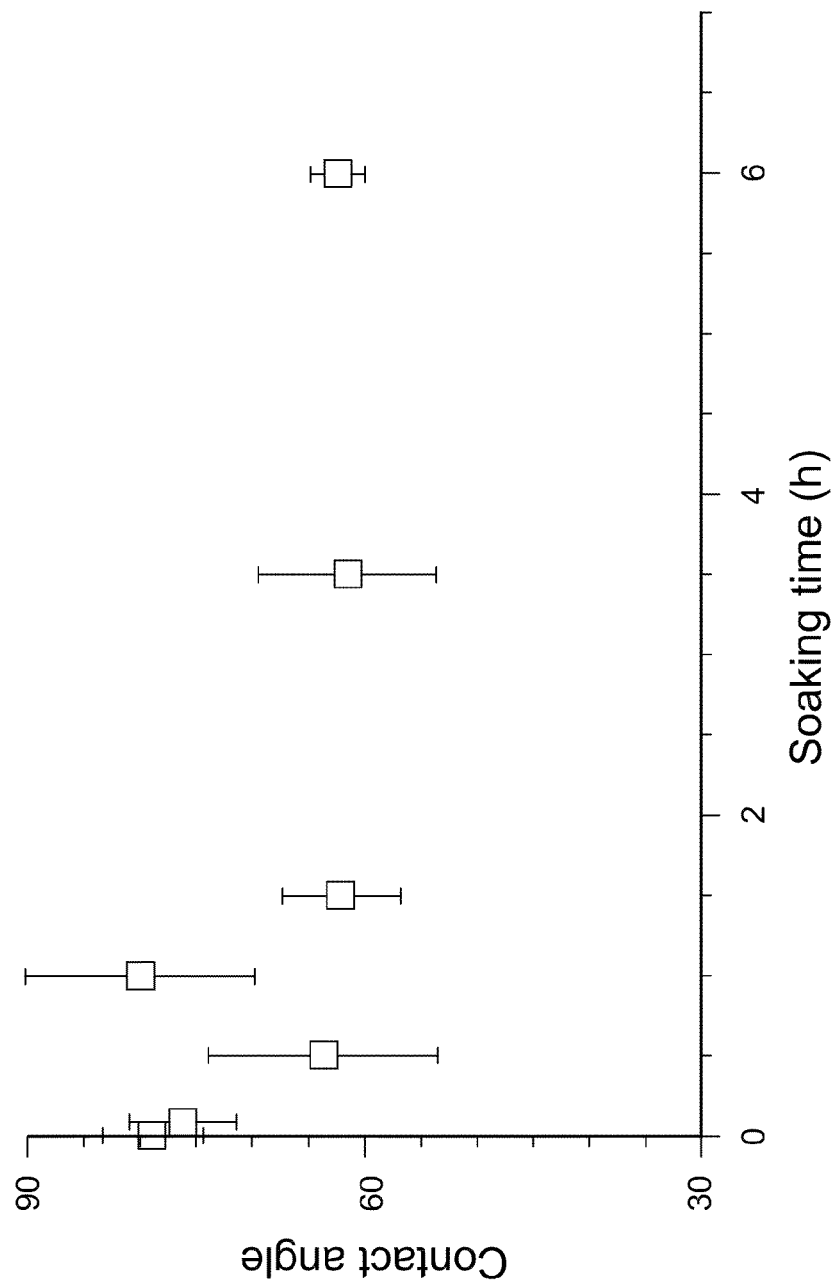
Figure 3C:
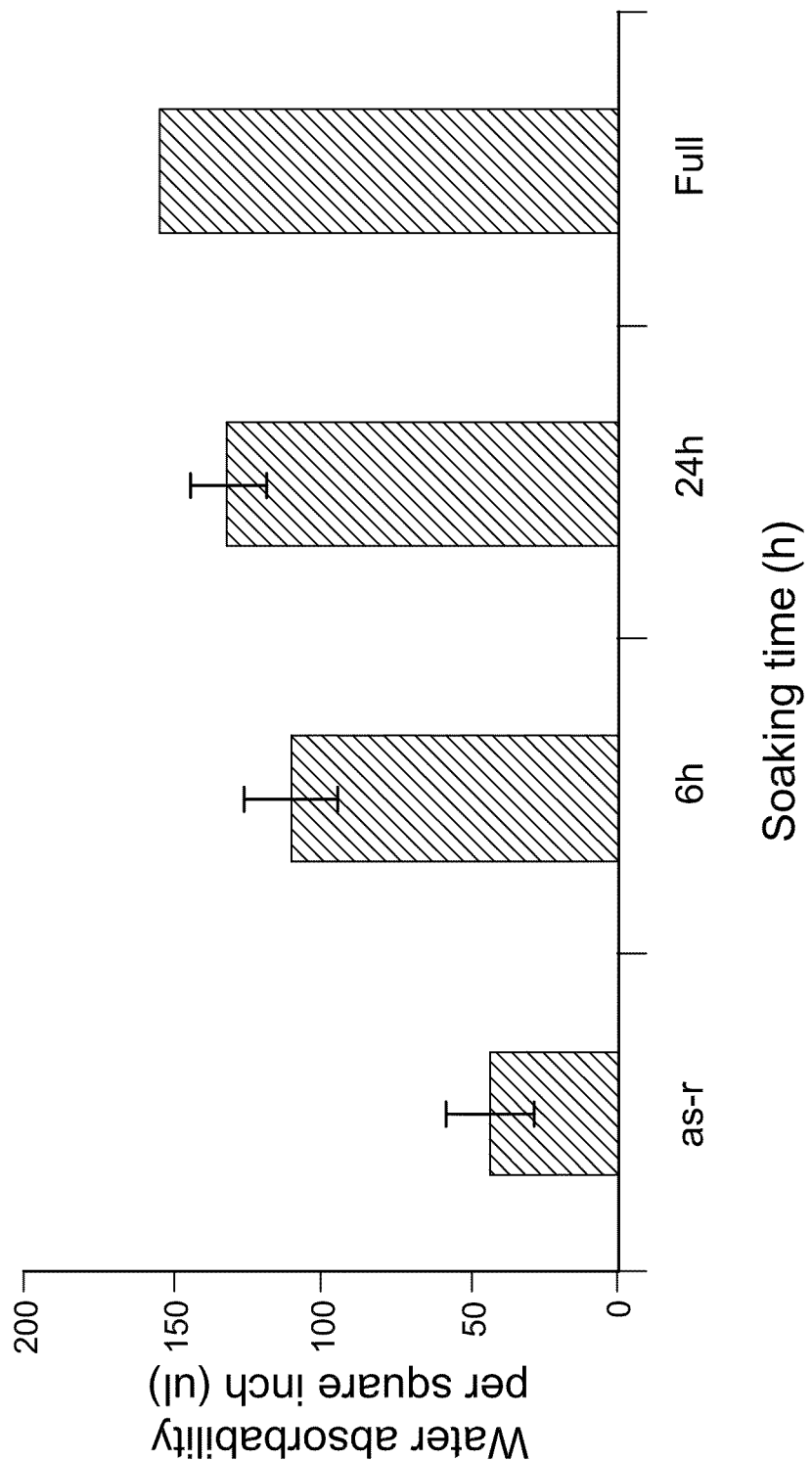

FIG. 3 shows (A) the weight loss per soaking time, (B) the contact angle of water placed on the surface of the disk versus soaking time, and (C) the water absorbability of the Porocoat® disk surface versus soaking time. The acid soaked Porocoat® disks absorbed significantly more water than untreated Porocoat® disks. The weight loss is determined by the difference between the disk measured prior to and after soaking The contact angle is measured by dosing one drop of 5 μl water on the ¾" wrought disk using standard contact angle measuring instrument and extracting the contact angle by applying the drop shape analysis. The same test was repeated for three times. The water absorbability is measured as described above.

Example 2

300 mL of the designated solution was added to a 500 mL beaker. A ¾" polished CoCrMo wrought disks was added to the beaker and allowed to lay flat with the polished surface facing up for 96 hours. The top of the beaker was sealed with Parafilm. After soaking, the disk was ultrasound cleaned. Disks soaked in 4N or 6N HCl were observed to show color change (slight blue) with disk surface losing its shininess (white cloudy areas appeared on the polished surfaces) but a disk soaked in 2N HCl for four days showed no color change in solution or surface change by appearance.

Example 3

Figure 4B:
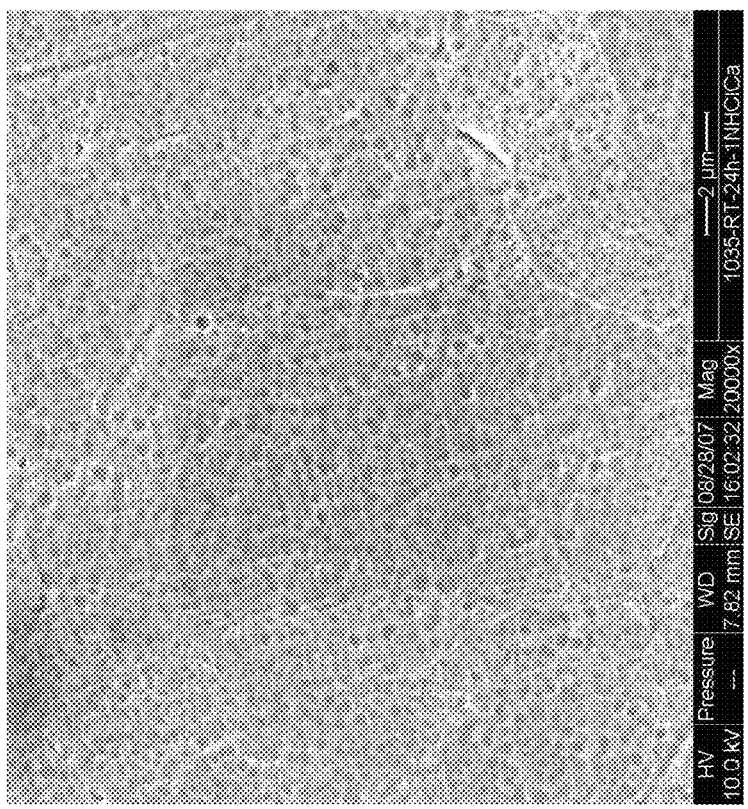
FIG. 4 shows (A) the morphologies of a ¾" (diameter) polished wrought CoCrMo disk after soaking in 1N HCl for 24 hours; and (B) of a ¾" (diameter) polished wrought CoCrMo disk after soaking in a chloride supplemented 1N HCl for 24 hours. The chloride supplemented 1N HCl is prepared by adding 70 g of $CaCl_2 \cdot 2H_2O$ in 100 ml of 1N HCl at room condition. The final concentrations in the chloride supplemented HCl acid are approximately [$H^+$]=0.8 N, [$Cl^-$]= 8.8 N, [$Ca^{2+}$]=4 N
Figure 4A:
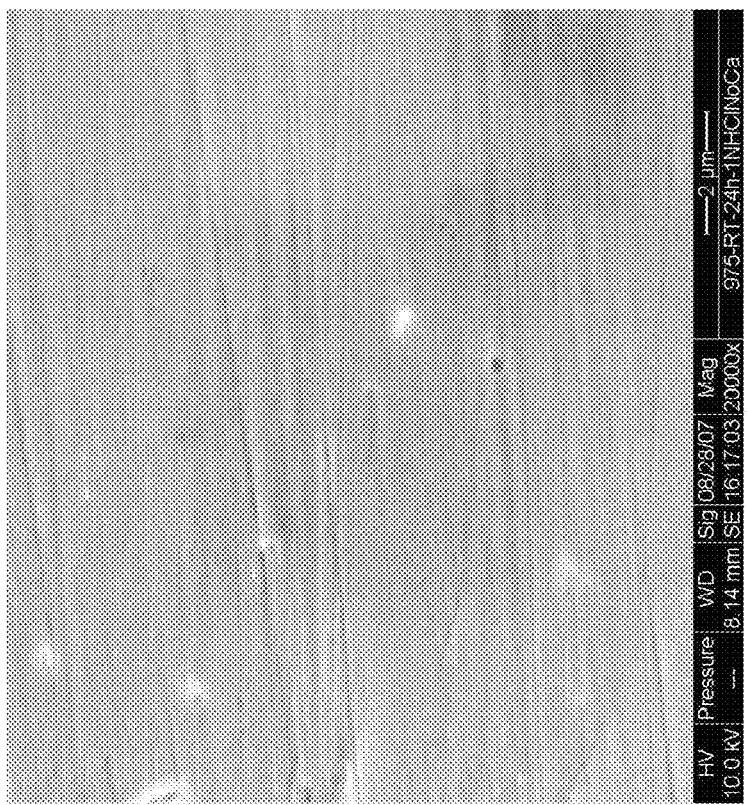

Two polished ¾" (diameter) wrought CoCrMo disks were fixed in one Teflon® fixture so that only one surface of each disk was exposed to acid. The two polished disks were soaked in 100 ml of the chloride supplemented HCl acid in a Pyrex glass container sealed by Parafilm® for 24 hours at room condition. Another two polished disks were fixed in a Teflon® fixture and soaked in 100 ml 1N HCl in a Pyrex® glass container sealed by Parafilm® for 24 hours at room condition. FIG. 4A shows the surface after soaked in 1N HCl for 24 hours and FIG. 4B shows the surface after soaked in chloride supplemented 1N HCl (solution 4)

The average weight loss per unit area exposed to the acid is 2.9±0.6 mg/in$^2$ for the disks soaked in chloride supplemented HCl acid and it is 0.5±0.2 mg/in$^2$ for the disks soaked in 1N HCl.

Example 4

Figure 5B:
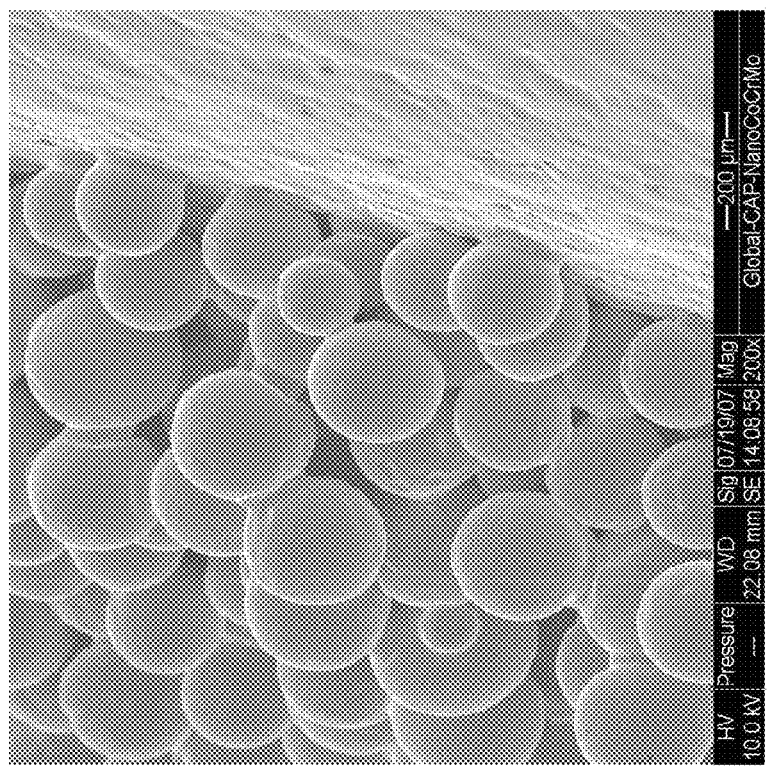
FIG. 5 shows (A) a lower magnification image of a Global CAP shoulder implant Porocoat® (CoCrMo) after soaking in acid for 24 hours; (B) a high magnification image of the pits ranging from 100 nm to 500 nm on the bead surface
Figure 5A:
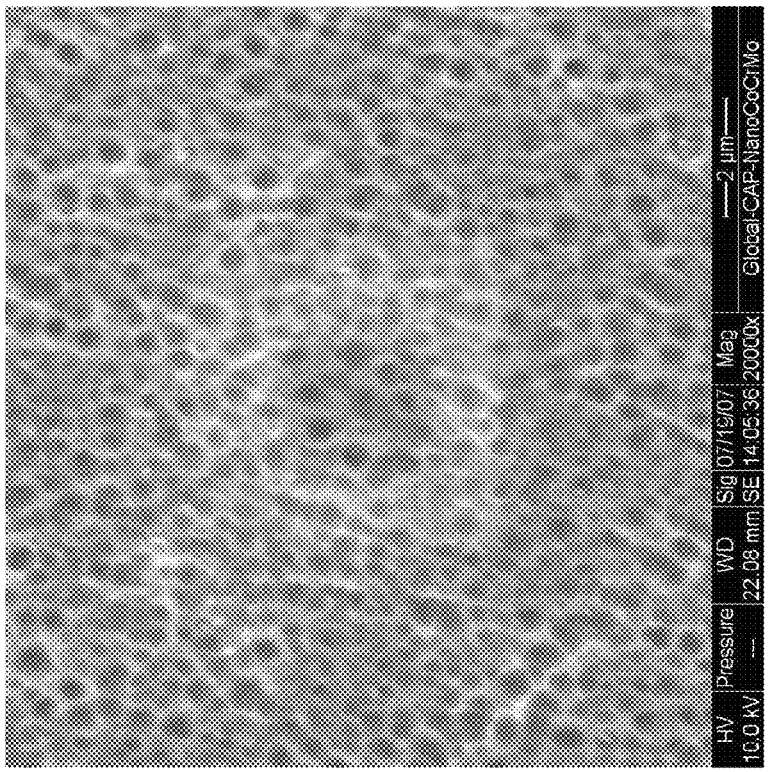

A Global CAP shoulder implant (FIG. 5A) was soaked in 300 ml 8N HCl solution for 24 hours at room condition in a Pyrex glass beaker sealed with parafilm. The implant was ultrasound cleaned after removal from the acid solution. Etched pits range from 100-500 nm can be observed on part or all of the bead surfaces (FIG. 5B).

What is claimed:

1. A process comprising contacting an article that includes cobalt chromium alloy with a solution consisting essentially of hydrochloric acid and a chlorine-containing compound selected from the group consisting of sodium chloride (NaCl), potassium chloride (KCl), calcium chloride (CaCl$_2$) and ammonium chloride (NH$_4$Cl) for a time and at a temperature effective to form a surface oxide layer on said article that has a thickness of 20 to 40 Å and is enriched in chromium relative to said article, wherein the article includes a plurality of indentions that independently have a diameter of from about 40 to about 500 nm, wherein said solution has a concentration of H$^+$ of at least about 0.8 N to about 12 N and a concentration of Cl$^-$ greater than the concentration of H$^+$.

2. The process of claim 1, wherein said chloride-containing compound is calcium chloride (CaCl$_2$).

3. The process of claim 1, wherein the article is contacted with the solution at a temperature of about 20 to about 100° C.

4. The process of claim 1, wherein the article is contacted with the solution at a temperature of about 20 to about 40° C.

5. The process of claim 1, wherein the article is contacted with the solution for about 30 minutes to about 96 hours.

6. The process of claim 1, wherein the cobalt-chromium alloy is CoCrMo.

7. The process of claim 1, wherein the surface of the article comprises cobalt-chromium alloy beads.

8. The process of claim 1, wherein the article is suitable for implantation into a mammal.

9. The process of claim 8, wherein said article is a joint replacement prosthesis or component thereof.

10. The process of claim 9, where said article is a hip or knee replacement prosthesis.

* * * * *